(12) United States Patent
Patel (10) Patent No.: US 11,612,719 B2
(45) Date of Patent: Mar. 28, 2023

(54) SYSTEMS OF CRAWLING CATHETERS WITH AUTOMATION ASSOCIATED PRODUCTS

(71) Applicant: VASOMETRICS, LLC, Lake Forest, CA (US)

(72) Inventor: Akshal Patel, Seattle, WA (US)

(73) Assignee: Akshal Patel, Seattle, WA (US)

( * ) Notice: Subject to any disclaimer, the term of this patent is extended or adjusted under 35 U.S.C. 154(b) by 954 days.

(21) Appl. No.: 16/468,376

(22) PCT Filed: Dec. 9, 2017

(86) PCT No.: PCT/US2017/065484
§ 371 (c)(1),
(2) Date: Jun. 11, 2019

(87) PCT Pub. No.: WO2018/107133
PCT Pub. Date: Jun. 14, 2018

(65) Prior Publication Data
US 2020/0009353 A1    Jan. 9, 2020

Related U.S. Application Data

(60) Provisional application No. 62/432,687, filed on Dec. 11, 2016.

(51) Int. Cl.
*A61M 25/01* (2006.01)
*A61B 34/30* (2016.01)
*A61M 25/00* (2006.01)

(52) U.S. Cl.
CPC .......... *A61M 25/0116* (2013.01); *A61B 34/30* (2016.02); *A61B 2034/301* (2016.02); *A61M 2025/0001* (2013.01)

(58) Field of Classification Search
CPC ............. A61B 34/30; A61B 2034/301; A61M 2025/0001; A61M 25/0116
See application file for complete search history.

(56) References Cited

U.S. PATENT DOCUMENTS

2009/0292296 A1* 11/2009 Pansky ............ A61B 17/22012
606/127
2011/0152880 A1*  6/2011 Alvarez ............ A61M 25/0147
606/130
2016/0029998 A1*  2/2016 Brister .................. A61F 5/0003
600/424

* cited by examiner

*Primary Examiner* — Jared Fureman
*Assistant Examiner* — Duc M Pham
(74) *Attorney, Agent, or Firm* — Patnstr ®, APC; Peter Jon Gluck, Esq.

(57) ABSTRACT

Novel catheter with longitudinal expandable arid contractile elements which promote wave propagation. The tension-band characteristics of these elements enhance the "crawling" dynamics of the catheter. Tauglit is an aspiration catheter with three key components: an inner spring coil system, a soft pleated jacket with annuli that buckles under load and an outer proleg or leaf-spring that fattens the. diameter of the catheter. Smart features, robotics and AI may be on-boarded. As shown, subject catheters shall piston in a fixed environment (muscular structure such as an artery) and propagate forward akin to earthworm locomotion (*Lumbricm terrestris*).

8 Claims, 4 Drawing Sheets

SYSTEMS OF CRAWLING CATHETERS WITH AUTOMATION ASSOCIATED PRODUCTS

FIELD

The present disclosure encompass most tubular medical devices which are designed to be temporarily or permanently emplaced within a lumen.

The present invention generally relates to catheters and more particularly to catheters used for various needs including for introduction and removal of fluids from a human body, further including automated, smart and peristaltically driven versions. Since the principles of operation shall be known to artisans, the example of an aspiration catheter is schematized and for simplicity of explanation is offered herein for consideration as an example as disclosed herein and as claimed below.

BACKGROUND OF THE DISCLOSURES

The teachings of nature offer solutions, albeit to problems different from what they were designed to express. By way of example, the common earthworm *Lumbricus terrestris*, propagates itself forward in a crawling dynamic never applied to a synthetic tubular body, according to the instant teachings—combined with the fact that currently, the Global Catheter Market in 2020 is projected to be the largest for any similar type of medical device because catheters are often the work-horse device and used with other systems, both as part of them and independently. Hence the teachings of this disclosure find contextual relevance.

By way of first example there are catheters that exist to aspirate thrombus or clot from arterial vessels, generally classified as "Aspiration Catheters", for the purposes of this matter, this includes any tubular structures used to drawn another group of substances through their lumens (in this case the "other substances" likewise may include prior failed devices, along with thrombus, etc.). They are not dynamic and remain in their tubular shape throughout their use. They come in various designs to maximize axial strength or pushability while retaining diameter and softness or trackability, to navigate safely in arterial vessels.

Within this application specialized alternate catheter systems are also described which can be adapted for use with the instant disclosure, as known to those of skill in the art. Regarding extent systems—in each case the limitation of this system is its lack of physiologic normalcy and the damage that can be precipitated by sub-atmospheric suctioning in an arterial.

Catheters are commonplace in the medical field, finding importance in a variety of uses. Catheters, for example, come in many different forms and have many different uses including Venous, Arterial, Cardiac, Urinary, Biliary, Epidural, Cerebral, Guiding, Pleural, Peritoneal, Ophthalmic, Drainage, Gastrointestinal, Neurovascular, Nasogastric. The primary types of vascular catheters include the short peripheral, which is typically placed only a short distance (e.g., 5-7.5 cm) in a vein or artery in the hand or arm of the patient, venous catheters that are longer and include a midline catheter that is placed approximately 15-20 cm in the vein of a patient, and central venous catheters.

Central venous catheters ("CVC") are typically used to administer medications, blood products, or other fluids and there are several types. Non-tunneled central venous catheters are commonly used for administration of therapeutics and fluids in critical care patients and are fixed in place at the site of insertion, with the catheter and attachments protruding directly. Tunneled catheters are passed under the skin from the insertion site to a separate exit site, where the catheter and its attachments emerge from the skin; a hemodialysis catheter is a commonly used type of tunneled central venous catheter. A peripherally inserted central catheter ("PICC") is commonly used for acute and chronic care patients and is inserted peripherally, e.g., in the arm of a patient rather than in the neck, chest or groin, and fed a significant distance, e.g., to the superior vena cava. Central venous catheters provide necessary vascular access but they are associated with two common complications; infection and thrombotic occlusion.

The pathogenesis of most catheter-related bloodstream infections associated with the use of long-term catheters (>10 days) involve microbial contamination of the catheter lumen(s), followed by formation of a microbial biofilm and subsequent seeding of the blood with microbial cells. Approximately 80,000 catheter-related blood stream infections occur in intensive care units each year (Mermel, *Ann. Intern. Med.* 132:391-402 (2000)) with an estimated 250,000 cases of blood stream infections occurring if entire hospitals are reviewed (Maki et al., *Mayo Clin. Proc.* 81:1159-71 (2006)). Cathether-related blood stream infections increase the cost of patient care by extending the length of stay of a patient.

Catheter occlusion is the most common non-infectious complication in long-term use of central venous catheters (Andris, 1999; Calis, Herbst, & Sidawy, 1999). Thrombotic occlusions, which include the development of a thrombus within and/or around the catheter or surrounding vessel (Haire & Herbst, 2000; Herbst & McKinnon, 2001), increase the cost of patient care by the interruption and extending the time of therapy, possible infiltration or extravasation of infusate, or as a nidus of infection. The incidence of thrombotic occlusion in central venous catheters ranges from 3% to 79% of inserted catheters (Moureau, Poole, Murdock, Gray, & Semba, 2002; Walshe, Malak, Eagan, & Sepkowitz, 2002; Wingerter, 2003).

Various methods have been proposed to prepare catheters with surfaces that express antimicrobial and/or antithrombogenic activity. Such methods include dip or spray coating of polymer/drug mixtures, drug impregnation, plasma coating, covalently bonded drugs, drug-polymer conjugates, and direct incorporation of the antimicrobial or antithrombogenic agents into the polymeric matrix of the catheter. Each of these methods present challenges with respect to catheter lumen surfaces such as one or more of the following: non-uniform coating thickness, inaccessible lumens, lumen blockage/restriction, require that only high heat tolerant agents can be used, and/or the limited duration of activity of drug reservoir-based systems, automating catheters also has not been contemplated with the state-of-the art in antibacterial and antimicrobial as described herein.

A vascular catheter typically consists of a hub and tubing or cannula through which fluid flows. Dependent on the type of catheter and its intended use, the number of tubes or cannula (lumen) through which fluid flows may range from one (monoluminal) to five or more; the more common are monoluminal, biluminal, or triluminal (1, 2 and 3 respectively). Typically, the different component parts (e.g., the hubs and tubing) are formed from different polymers. This presents challenges to create a single surface modification with similar properties across at least two catheter components, and to automate any portions which are automated and may optionally include pressure and aspiration management modules, as defined below.

There exists a need for techniques and catheters that can be effective at reducing microbial contamination/biofilm and thrombus attachment and accumulation on a catheter.

OBJECTS AND SUMMARY OF THE INVENTION

Briefly stated, a catheter with longitudinal expandable and contractile elements which promote wave propagation. The tension-band characteristics of these elements enhance the "crawling" dynamics of the catheter.

From the example of an aspiration catheter each element has three key components: an inner spring coil system, a soft pleated jacket with annuli that buckles under load and an outer proleg or leaf-spring that fattens the diameter of the catheter. The catheter is to be used with a variable aspirator that causes the catheter to oscillate along the axis of the catheter. In a fixed hydrostatic system, the catheter will piston in a muscular structure such as an artery and propagate itself forward akin to earthworm locomotion (*Lumbricus terrestris*).

According to embodiments of the disclosure there is presented a catheter having longitudinal expandable and contractile elements, comprising, in combination; at last an inner coil spring system; soft-pleated jacket means for building; and an outer mechanism for managing catheter diameter, along a variable pumping and aspirating aspects optionally included.

According to embodiments there is offered for consideration a pleated jacket means having at least an inner surface coated with a lubricous silicone composite material.

According to embodiments there is offered for consideration an improved system comprising in combination; employing plateaus of negative pressure and positive pressure; using low and high frequency variance changes, whereby said delta frequency values can govern or preselected any programmed aspects of movement versus break-up of occlusion material to be aspirated.

According to embodiments there is offered for consideration any number of Medical devices for relieving occlusion events working with the instant systems comprising stents, stent-retriever and stenting means, combinations, balloons, bio-resorbable assemblies, separators and other vascular tools.

According to embodiments there is offered for consideration several devices such as novel Enhanced contractomeres comprising; in combination, nodes incorporated into a catheter or similar material device further comprising, a coiled spacing emplaced against a wall as single or doubled helical configuration, a pleated jacket, matching the helical or screen pitch of the spacings; and a proleg extension of the non-contractomeres, or fixed component of the catheter involved the jacket and spacing.

According to embodiments there is offered for consideration there are disclosed at least a contractomere wherein the coiled spacing comprises stainless steel and stores energy during negative vacuum.

According to embodiments there is offered for consideration contractomeres, further comprising biocompatible polymers forced with Nitinol® braids to provide strain relief and reduce inherent kinkage.

According to embodiments shown and described and illustrated herein there is disclosed a process, wherein during periods of "rest" or non-aspiration conditions, the proleg is flush with the main catheter and appears as a longitudinally vertebrated portion of the main catheter. During collapse of the contractomere, under axial load, the proleg components bend outward, fattening the diameter of the catheter.

According to embodiments thee is disclosed a catheter system wherein he frequency of the aspiration wave can vary to augment or retard the inching of the catheter. There can be plateaus of negative pressure or positive pressure at the discretion of the operator. A low and high frequency variance changes the activity of the catheter. Low frequencies are more likely to cause forward progress, high frequencies are more likely to cause break-up of occlusive materials at the end of the catheter.

The catheter will be used as a platform for other devices deployed or in preparation for deployment in the artery. In the setting of occlusion: stents, retrievers, stent-retrieving combinations, balloons and separators can all be used in concert with the invention. These devices, commonly used in stroke and pulmonary embolism, will act as distal anchors for the "crawling" catheter. During catheter motion, it will invest and ingest the occlusive material, and ride over the anchoring devices to envelope them as well.

The advantages of this catheter are related to its use in the vascular system. Where the peristalsis of the catheter generates an atraumatic anterograde advancement. Inside the muscular artery this retains a physiologic profile in the setting of aspiration or retrieval of occlusive materials. Traditional catheters act as fixed tubular skeletons and can create force vectors that damage vessel lumens. The invention is modular and takes into account the elastic property of the artery wall.

Among the various aspects of the present invention is the provision of catheters comprising a polymeric material which are automated and may optionally include on the exterior and/or intraluminal surfaces thereof that can be effective at reducing microbial attachment, biofilm formation, platelet attachment or thrombus formation.

Other objects and features will be in part apparent and in part pointed out hereinafter.

BRIEF DESCRIPTION OF THE DRAWINGS

Corresponding reference characters have either been used, for example for the novel catheter itself and also have been omitted owing to the schematic nature of the embodiments disclosed there being no strict need to indicate corresponding parts throughout the drawings, as known to artisans.

Abbreviations and Definitions

The following definitions and methods are provided to better define the present invention and to guide those or ordinary skill in the art in the practice of the present invention. Unless otherwise noted, terms are to be understood according to conventional usage by those of ordinary skill in the relevant art.

When introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

Biocompatibility: unless otherwise indicated, "biocompatibility" is the ability of a material to perform with an appropriate host response in a specific situation. This can be evaluated using International Standard ISO 10993. Biocompatible compositions described herein are preferably substantially non-toxic.

Brushes/Polymer Brushes: unless otherwise indicated, "brushes" or "polymer brushes" are used herein synonymously and refer to polymer chains that are bound to a surface generally through a single point of attachment using graft-from techniques. The polymers can be end-granted (attached via a terminal group) or attached via a side chain or a position in a polymer chain other than a terminal position. The polymers can be linear or branched. For example, the polymer chains described herein can contain a plurality of side chains that contain zwitterionic groups. The side chains can consist of a single non-fouling moiety or monomer and/or a non-fouling oligomer (e.g., 2-10 monomeric residues) or a polymer (e.g., >10 monomeric residues).

Catheter: is commonly used to identify a tubular instrument that is inserted into a human body cavity or orifice, naturally or surgically opened.

Catheter substrate: unless otherwise indicated, a "catheter substrate" is a catheter or one or more components thereof, such as a catheter body, juncture hub, extension line or connector.

Coating: unless otherwise indicated, "coating" refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate.

Figure 1:
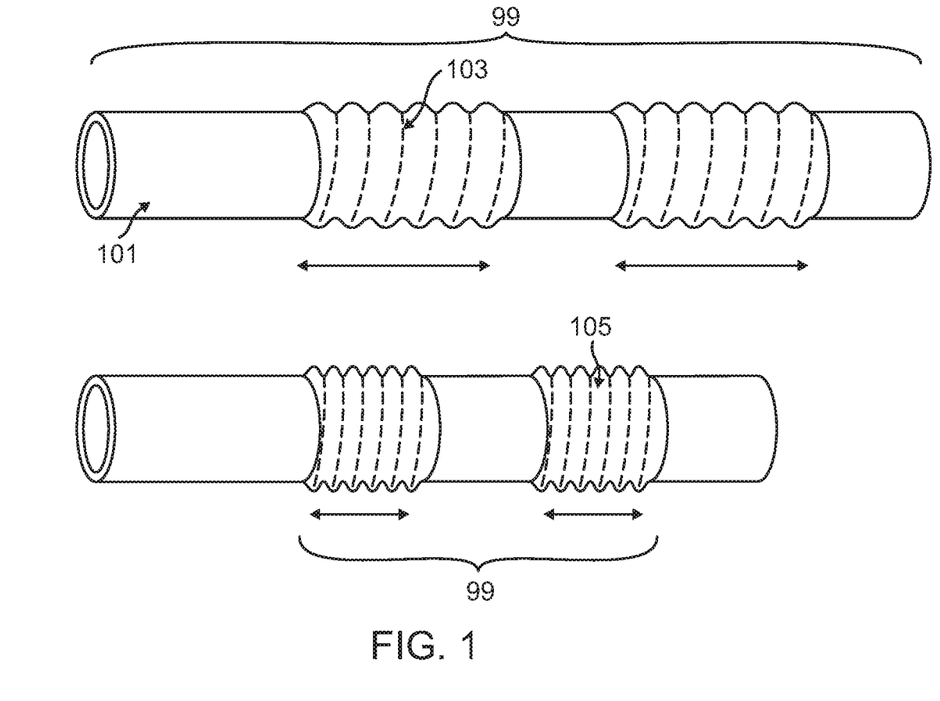
FIG. 1 is a perspective view of a schematic of an exemplary catheter in accordance with embodiments.

Contractomere is defined for the purposes of this invention as a modular functional unit capable of facilitating relative movement from a first to a second position as shown, for example by the two sets of arrows in the first figure—exemplary embodiments shown are not meant to be limiting and those skilled in the art understand that, for example, prolegs 232 and their functional equivalents such as stent-like structures may be substituted based on functional homologous, inter Alia.

Degradation Products: unless otherwise indicated, "degradation products" are atoms, radicals, cations, anions, or molecules other than water formed as a result of hydrolytic, oxidative, enzymatic, or other chemical processes.

The term "distal" refers to a direction relatively furthest from a clinician using a catheter described herein. For example, the end of a catheter placed within the catheter body of a patient is considered a distal end of the catheter, while the catheter body of a patient is considered a distal end of the catheter, while the catheter end remaining outside the catheter body is a proximal end of the catheter.

Hydrophilic: unless otherwise indicated, "hydrophilic" refers to solvents, molecules, compounds, polymers, mixtures, materials, or functional groups which have an affinity for water. Such materials typically include one or more hydrophilic functional groups, such as hydroxyl, zwitterionic, carboxy, amno, amide, phosphate, sulfonyl, hydrogen bond forming, and/or ether groups.

Hydrophobic: unless otherwise indicated, "hydrophobic" refers to solvents, molecules, compounds, polymers, mixtures, materials, or functional groups that are repelled by water. Such materials typically contain non-polar functional groups.

The term "proximal" refers to a direction relatively closer to a clinician using a catheter described herein. For example, the end of a catheter placed within the body of a patient is considered a distal end of the catheter, while the catheter end remaining outside the body is a proximal end of the catheter.

Tip Region: unless otherwise indicated, "Tip Region," as used herein, shall mean the terminal 10 cm length of the catheter body at the distal end of the catheter body.

Undercoating Layer: unless otherwise indicated, "undercoating layer" refers to any coating, or combination of coatings, incorporated into a substrate from which a hydrophilic polymer is grafted.

DETAILED DESCRIPTION OF THE PREFERRED EMBODIMENTS

The present invention applies variable segments which are contractile to any known catheter system, in combination with fixed segments, whereby collapsible nodes enable movement of catheter 99.

The catheter body may be fabricated from any of a range of biocompatible polymers. For example, in certain embodiments the catheter body may be comprised of thermoplastic polyurethanes ("TPU"), thermoplastic polyurethane-silicones, silicones, or a combination thereof. Exemplary polyurethanes include Lubrizol Tecothane®, Lubrizol Carbothane®, Lubrizol Tecoflex®, Lubrizol Pellethane®, Lubrizol Estane®, Bayer Desmopan®, Bayer Texin®, DSM Bionate®, DSM Biospan®, DSM Bionate® II, DSM Elasthane®, BASF Elastollan™, Biomerics Quadrathane™, Biomerics Quandraflex™, Biomerics Quadrahilic™, or a blend thereof, in a range of hardnesses from 100 A to 80 A durometer. Alternatively, exemplary polyurethanes will have a range of hardnesses from 70 A to 72 D. Exemplary polyurethane-silicones include AorTech Elast-Eon™, AorTech ECSil™, DSM CarboSil®, DSM Pursil®, or a blend thereof in a range of hardnesses from 80 A to 60 D durometer. Alternatively, exemplary polyurethane-silicones will have a range of hardnesses from 70 A to 72 D. Exemplary silicones include peroxide-cured and platinum cured silicones in a range of hardnesses from 50 A to 60 D durometer. Alternatively, exemplary silicones will have a range of hardnesses from 50 A to 70 D. Additionally, the biocompatible polymer may optionally contain a radiopacifier such as barium sulfate, bismuth trioxide, bismuth subcarbonate, bismuth oxychloride, tungsten, or tantalum, or a combination thereof. If included, the radiopacifier will typically be added at 5 wt % to 40 wt %. Colorants may also be included in the biocompatible polymer and the catheter body would then be opaque.

Referring now to the figures showing an aspiration catheter example, wherein FIG. 1 is a perspective view of a catheter 99 in accordance with one embodiment. The catheter shown is a fixed segment molded to the vessel and there are variable contractile segments or contractomeres, 103 shown is a first position, which moves to a second position 105 advancing the catheter like the movement of a common earthworm.

Each node moves from a first to a second position and allows the catheter to move axially. This version works well for high viscosity slurry types of materials.

Wave proportion and crawling are achieved as would be known by those skilled in the art.

Figure 3:
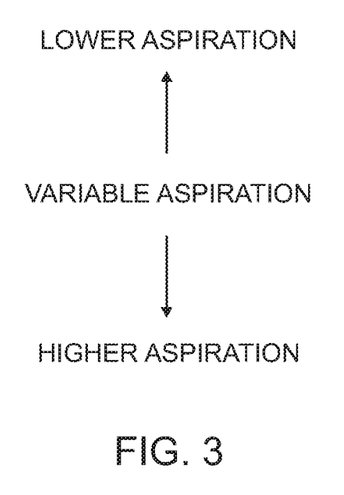
FIG. 3 shows how another, this time graphical representation of pressure v. aspiration in embodiments of the present invention.
Figure 4:
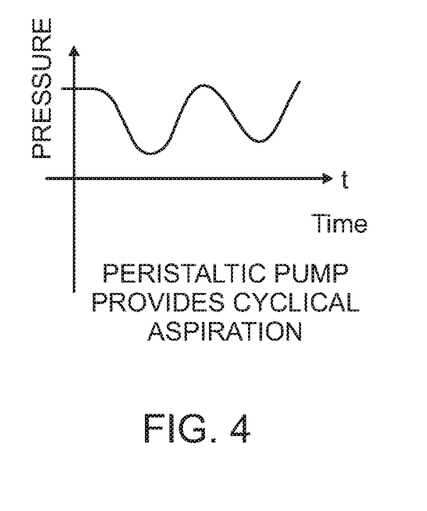
FIG. 4 shows the sinusoidal mechanism of action of a described embodiment of a peristaltic pump, useful with the present invention outside of the scope of some claimed embodiments.

Similarly, FIG. 3 shows contractomeres 103/105 and is a graphical representation of pressure v. aspiration in embodiments of the present invention; and FIG. 3 shows the sinusoidal mechanism of action of a described embodiment of a peristaltic pump.

Figure 2A:
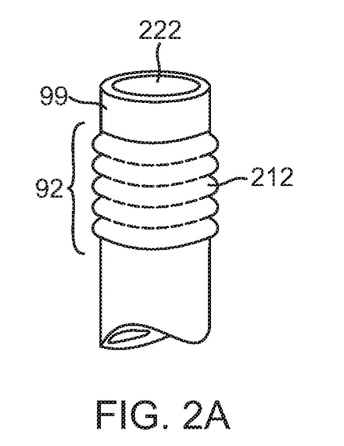
FIG. 2A is a schematic of a basic contractomere device according to embodiments of the present invention.
Figure 2B:
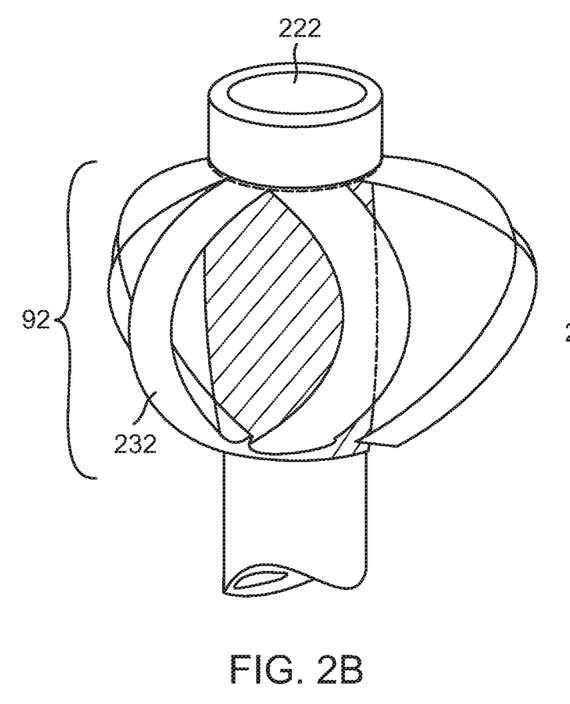
FIG. 2B shows further details of embodiments of devices and systems according to the present inventions.
Figure 2C:
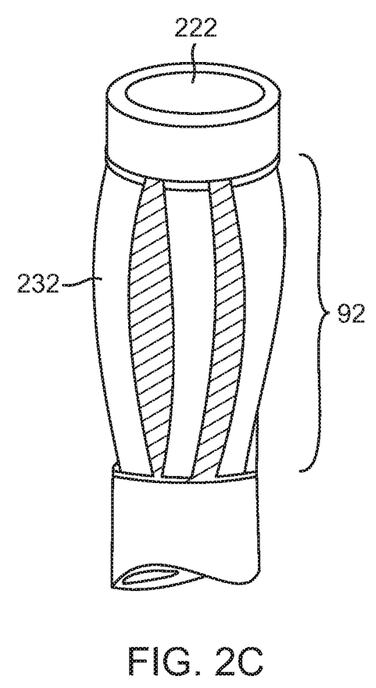
FIG. 2C shows a second position of the device according to figures preceding it.

Referring now to example embodiments of FIGS. 2A, 2B and 2C, there are at least two key working elements of this invention. The first is the expansible and contractile nodes of the catheter which will be referred to as contractomeres. The second is the aspiration mechanism which will provide a sinusoidal positive and negative pressure to allow the catheter to ingest highly viscous slurry materials, such as clot.

Contractomeres 92 are designed with three elements. FIG. 2 shows how a coiled spring (not shown) sits in the wall and can be made up in a single or double helical configuration. It is made of stainless steel and will store energy during negative vacuum. The second is the pleated jacket 212, which can match the helical or screw pitch of the spring. It is constructed of a biocompatible polymer such as polyethylene and will be reinforced with Nitinol braids to provide strain relief and reduce kinkability. The inner surface of 212 (not shown) is coated with silicone composite material to make it lubricious. The jacket is to deform and collapse under axial load much like an accordion. The third and outermost component is the proleg 232, which is an extension of the non-contractomere or fixed component of the catheter which envelopes the jacket and spring. Proleg 232 is a leaf-spring that bends outward and can temporarily anchor the catheter to the inner lumen of the vessel wall.

During periods of "rest" or non-aspiration conditions, proleg 232 is flush with the main catheter 99 and appears as a longitudinally vertebrated portion of the main catheter. During collapse of the contractomere 92, under axial load, proleg 232 components bend outward, fattening the diameter of the catheter.

The contractomere's jacket and spring are made separately and later bonded to the catheter. The proleg is made by barrel staving the catheter along its axis. Each contractomere is calibrated to displace at a specific force and thus a unique kinomatic profile, though there is overlap of activation of each contractomere during an aspiration cycle.

In the setting of an occluded artery, the catheter will sit in close proximity to the obstruction. With this arrangement the artery and catheter together act as a fixed hydrostatic system, with a relatively unchanged fluid volume. With cyclical aspiration, the catheter will inch toward the occlusion.

The aspiration mechanism is a device that is attached directly or indirectly to the end of the catheter. It will provide sinusoidal vacuum forces that will cause repetitive loading and unloading of forces on the contractomere. The frequency of the aspiration wave can vary to augment or retard the inching of the catheter. There can be plateaus of negative pressure or positive pressure at the discretion of the operator. A low and high frequency variance changes the activity of the catheter. Low frequencies are more likely to cause forward progress, high frequencies are more likely to cause break-up of occlusive materials at the end of the catheter.

The catheter will be used as a platform for other devices deployed or in preparation for deployment in the artery. In the setting of occlusion: stents, retrievers, stent-retrieving combinations, balloons and separators can all be used in concert with the invention. These devices, commonly used in stroke and pulmonary embolism, will act as distal anchors for the "crawling" catheter. During catheter motion, it will invest and ingest the occlusive material, and ride over the anchoring devices to envelope them as well.

The advantages of this catheter are related to its use in the vascular system. Where the peristalsis of the catheter generates an atraumatic anterograde advancement. Inside the muscular artery this retains a physiologic profile in the setting of aspiration or retrieval of occlusive materials. Traditional catheters act as fixed tubular skeletons and can create force vectors that damage vessel lumens. The invention is modular and takes into account the elastic property of the artery wall.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Reference throughout this specification to "one embodiment," "an embodiment," or similar language mans that a particular feature, structure, or characteristic described in connection with the embodiment is included in at least one embodiment of the present invention. Thus, appearances of the phrases "in one embodiment," "in an embodiment," and similar throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks): and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A system for automatically moving axially a catheter within a lumen which comprises, in combination: a specialty catheter having longitudinal expandable and contractile elements, further comprising, in combination: at least an inner coil spring system; soft-pleated jacket means for buckling; and, an outer mechanism for managing catheter diameter; along with a variable pumping aspect optionally included; wherein a final third and outermost component is a proleg, which is an extension of a non-contractomere or fixed component of the catheter which envelopes the jacket and spring, the proleg is a leaf-spring that bends outward and can temporarily anchor the catheter to the inner lumen of the vessel wall whereby each contractomere is calibrated to displace at a specific force and thus a unique kinematic profile, though there is an overlap of activation of each contractomere during an aspiration cycle.

2. The system of claim 1, wherein the aspiration mechanism is a device that is attached directly or indirectly to the end of the catheter, which shall provide sinusoidal vacuum forces that will cause repetitive loading and unloading forces on said contractomere.

3. The system of claim 2, wherein the frequency of the apsiration wave can vary to augment or retard the inching of the catheter, meaning there can be plateaus of negative or positive pressure at the discretion of the operator, and a low and high
frequency variance changes the activity of the catheter, low frequencies are more likely to cause forward progress.

4. A process for advancing and stopping catheters, having embedded contractomeres comprising, in combination:
employing plateaus of negative pressure and positive pressure;
using low and high frequency variance changes; whereby said delta frequency values can balance Movement; the process comprising in combination:
at least two nodes incorporated into a catheter or similar material devices further comprising:
a coiled spring emplaced against a wall as single or double or multiple helical configuration;
a pleated jacket, matching the helical or screen pitch of the spacings; and, a proleg extension of the non-contractomeres, or fixed component of the jacket and spacing.

5. A process for advancing and stopping catheters, having embedded contractomeres comprising in combination:
employing plateaus of negative pressure and positive pressure;
using low and high frequency variance changes;
whereby said delta frequency values can balance movement, the process comprising in combination:
at least two nodes incorporated into a catheter or similar material device further comprising:
a coiled spring emplaced against a wall as a single or double or multiple helical configuration;
a pleated jacket, matching the helical or screen pitch of the spacings;
a proleg extension of non-contractomeres, or fixed component of the jacket and spacing, wherein the coiled spacing comprises stainless steel and stores energy during negative vacuum.

6. A process for advancing and stopping catheters having embedded contractomeres comprising in combination:
employing plateaus of negative and positive pressure;
using low and high frequency variance changes;
whereby said delta frequency values can balance movement, the process comprising combination:
at least two nodes incorporated into a catheter or similar material device further comprising:
a coiled spring emplaced against a vessel wall as a single or double or multiple helical configuration;
a pleated jacket, matching the helical or screen pitch of the spacings;
a proleg extension of non-contractomeres, or fixed component of the jacket and spacing, wherein the coiled spacing comprises stainless steel and stores energy during negative vacuum;
further comprising biocompatible polymers reinforced with NITINOL braids to prove strain relief and reduce kinkability.

7. A system for automatically moving axially a catheter within a lumen which comprises, in combination:
A specialty catheter having longitudinal expandable and contractile elements, further comprising in combination:
at least an inner coil spring system;
soft-pleated jacket means for buckling; and an outer mechanism for managing catheter diameter; along with a variable pumping aspect optionally included; wherein a final third and outermost component is a proleg, which is an extension of a non-contractomere or fixed component of the catheter which envelopes the jacket and spring, the proleg is a leaf-spring that bends outward and can temporarily anchor the catheter to the inner lumen of the vessel wall whereby each contractomere is calibrated to displace at a specific force and thus a unique kinematic profile, though there is overlap of activation of each contractor during an aspiration cycle; wherein the aspiration mechanism is a device that is attached directly or indirectly to the end of the catheter, which shall provide sinusoidal vacuum forces that will cause repetitive loading and unloading of forces on said contactomere further comprising at least a sensor and microelectronics support communicating into a database.

8. The system of claim 7, wherein logic gating and resource allocation is governed by AI, via means which are embedded, wirelessly linked, on boarded or otherwise in communication with said system.

* * * * *